United States Patent [19]
Nique

[11] Patent Number: 6,005,003
[45] Date of Patent: Dec. 21, 1999

[54] DERIVATIVES OF DIHYDRO OR TETRAHYDRONAPHTHALENE, AND THE PHARMACEUTICAL COMPOSITIONS CONTAINING THEM

[75] Inventor: Francois Nique, Le Perreux sur Marne, France

[73] Assignee: Hoechst Marion Roussel, France

[21] Appl. No.: 09/305,620

[22] Filed: May 5, 1999

[30] Foreign Application Priority Data

May 6, 1998 [FR] France .................................. 98 05709

[51] Int. Cl.⁶ ............................ C07C 57/42; A61K 31/19
[52] U.S. Cl. .................... 514/532; 514/569; 514/622; 549/406; 560/56; 562/466; 564/172
[58] Field of Search ................................ 560/56; 562/466; 564/172; 549/406; 514/532, 569, 622

[56] References Cited

U.S. PATENT DOCUMENTS 5,552,412  9/1996  Cameron et al. .

FOREIGN PATENT DOCUMENTS 9732837  9/1997  WIPO .

OTHER PUBLICATIONS

Willson et al, 3–[4–(Diphenylbut . . . Uterus in Rats, Journal of Medicinal Chemistry, vol. 37, No. 11, May 27, 1994, pp. 1550–1553.

*Primary Examiner*—Robert Gerstl
*Attorney, Agent, or Firm*—Bierman, Muserlian and Lucas

[57] ABSTRACT

A subject of the invention is the compounds of general formula (I):

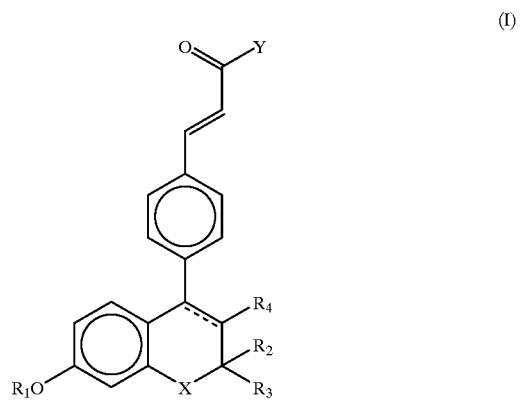

in which R1=H, alkyl, acyl, R2 and R3=H, alkyl, R4=aryl, heteroaryl, X=O, CH2, Y=OH, O-alkyl or NRaRb, as well as the salts, their preparation processes, the intermediates of these processes, their use as medicaments and the pharmaceutical compositions containing them.

8 Claims, No Drawings

DERIVATIVES OF DIHYDRO OR TETRAHYDRONAPHTHALENE, AND THE PHARMACEUTICAL COMPOSITIONS CONTAINING THEM

A subject of the present invention is derivatives of dihydro or tetrahydronaphthalene, their preparation processes and intermediates, their therapeutic use and the pharmaceutical compositions containing them.

Osteoporosis is a pathology which is characterized by a quantitative and qualitative reduction in bone matter, sufficient to lead to vertebral or peripheral fractures, in a spontaneous fashion or on occasions due to minimal traumas.

Although this illness has many factors at its origin, it is the menopause, which in woman, constitutes the dominating factor in bone loss or osteopenia.

This osteopenia manifests itself by a rarefaction and a modification of the architecture of the spongy bone the consequence of which is to increase the fragility of the skeleton and the risk of fractures. Bone loss increases strongly after the menopause due to the suppression of ovarian function and reaches 3 to 5% per year before slowing down after 65 years of age.

For a therapeutic purpose, the post-menopause hormonal deficiency can be compensated for by a hormone replacement therapy where oestrogen plays a major role in preserving the bone mass. But long-term oestrogenotherapy is sometimes accompanied by undesirable effect on the genital apparatus (endometrial hyperplasia, breast tumors etc.), which constitutes a major drawback and limits its use.

It is therefore convenient to find compounds other than oestradiol having a dissociated oestrogen activity, namely an oestrogen activity at the bone level, while having none or little of the endometrial hyperplasia activity, nor breast tumor proliferation activity.

Therefore a subject of the invention is the compounds of general formula (I):

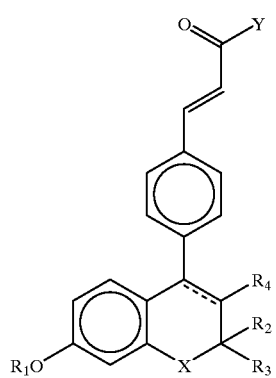

(I)

in which:
R1 represents a hydrogen atom, an alkyl radical or an acyl radical,
R2 and R3, identical or different, represent a hydrogen atom, an alkyl radical, or together form a cyclo alkyl containing from 3 to 7 carbon atoms,
R4 represents an aryl or heteroaryl radical,
X represents O or CH2,
Y represents a hydroxy, alkyloxy radical or an NRaRb group in which:
either Ra and Rb, identical or different, represent a hydrogen atom or an alkyl radical, or Ra and Rb form together with the nitrogen atom to which they are linked a mono or polycyclic heterocycle with 3 to 15 members optionally containing an additional heteroatom chosen from oxygen, sulphur and nitrogen, said alkyl, alkyloxy and acyl contain 1 to 6 carbon atoms, said alkyl, acyl, aryl and heterocycle are substituted or non substituted, the dotted line optionally represents a double bond, the compounds of formula (I) being able to be in all their possible stereoisomeric forms, isolated or in mixtures, as well as the addition salts with acids or bases.

By alkyl containing from 1 to 6 carbon atoms, is meant the methyl, ethyl, propyl, isopropyl, butyl, isobutyl, tert-butyl, n-pentyl, n-hexyl, 2-methyl pentyl, 2,3-dimethylbutyl radicals.

By acyl containing from 2 to 6 carbon atoms is meant in particular the acetyl, propionyl and butyryl radicals.

By aryl radical is preferably meant the phenyl or naphthyl group.

By heteroaryl (or aromatic heterocycle) radical, is preferably meant the thienyl, furyl, isothienyl, isofuryl, thiazolyl, isothiazolyl, oxazolyl, thiadiazolyl, pyridinyl groups.

By alkyloxy radical containing from 1 to 6 carbon atoms, is preferably meant the methoxy, ethoxy, propyloxy, isopropyloxy and butyloxy radicals.

When Ra and Rb form together with the nitrogen atom to which they are linked a saturated heterocycle, in particular it is the following mono or bicyclic heterocycles:

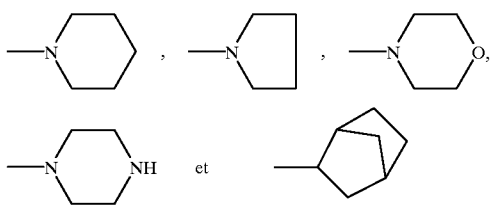

When the alkyl, acyl, aryl or heterocycle (aromatic or not) radicals are substituted, they can be in particular by the following radicals:
halogen, namely fluorine, chlorine, bromine or iodine, alkoxy such as methoxy, ethoxy, propyloxy, isopropyloxy, butyloxy, alkylthio such as methylthio, ethylthio, propylthio, isopropylthio, butylthio, amino, alkylamino such as methylamino or ethylamino, dialkylamino such as dimethylamino, diethylamino, methylethylamino, each of these dialkylamino radicals being optionally in oxidised form, aminoalkyl such as aminomethyl or aminoethyl, dialkylaminoalkyl such as dimethylamino methyl or ethyl, dialkylaminoalkyloxy such as dimethylamino ethyloxy, hydroxyl optionally acylated, acyl such as acetyl, propionyl, butyryl, benzoyl, free, esterified carboxy such as alkoxy carbonyl for example methoxy carbonyl or ethoxy carbonyl, cyano, trifluoromethyl, aryl such as phenyl, aralkyl such as benzyl, alkyl, alkenyl or alkynyl these radicals being themselves optionally substituted by the halogen, alkyl, alkoxy, alkylthio, amino, alkylamino or dialkylamino radicals indicated above.

Of course, the expression "substituted" indicates that one or more substituents, identical or different, can be present. By way of an example, when the alkyl group is a methyl radical substituted by one or more halogen atoms, it can be in particular $CH_2Cl$, $CH_2F$, $CHF_2$ and $CF_3$.

The invention naturally extends to the salts of the compounds of formula (I), such as for example the salts formed with mineral or organic acids on the amine. Thus it can be one of the following acids: hydrochloric, hydrobromic, nitric, sulphuric, phosphoric, acetic, formic, propionic, benzoic, maleic, fumaric, succinic, tartaric, citric, oxalic, glyoxylic, aspartic, alkane sulphonics such as methane or ethane sulphonics, arylsulphonics, such as benzene or para-toluene sulphonics and arylcarboxylics. When the compounds of formula (I) contain an acid function, the invention extends to salts of alkali, alkaline-earth metals or ammonium optionally substituted.

A more particular subject of the invention is the compounds of formula (I) as defined above in which: R1, R2 and R3 are hydrogen atoms, R4 is a substituted or non substituted phenyl and Y represents a hydroxy, alkyloxy radical containing from 1 to 6 carbon atoms or NRaRb, Ra and Rb each representing an alkyl radical containing from 1 to 6 carbon atoms.

A more particular subject of the invention is also the compounds of formula (I) as defined previously in which the R4 and Ph—CH═CH—COY groups are in cis position.

A quite particular subject of the invention is the following compounds:
3-[4-(3,4-dihydro-6-hydroxy-2-phenyl-1-naphthalenyl) phenyl] 2-propenoic acid,
(+,−) cis 3-[4-(6-hydroxy-2-phenyl-1,2,3,4-tetrahydro-1-naphthalenyl)phenyl] 2-propenoic acid,
(+,−) cis N,N-diethyl-3-[4-(6-hydroxy-2-phenyl-1,2,3,4-tetrahydro-1-naphthalenyl)phenyl] 2-propenamide,
ethyl 3-[4-(3,4-dihydro-6-methoxy-2-(4-methoxyphenyl)-naphthalenyl)phenyl] 2-propenoate,
ethyl 3-[4-(3,4-dihydro-6-hydroxy-2-(4-hydroxyphenyl) 1-naphthalenyl)phenyl] 2-propenoate,
3-[4-(3,4-dihydro-6-hydroxy-2-(4-hydroxyphenyl)-naphthalenyl)phenyl] 2-propenoic acid,
3-[4-(6-methoxy-2-(4-methoxyphenyl) 3,4-dihydro 1-naphthalenyl)phenyl] 2-propenoic acid,
N,N-diethyl 3-[4-[3,4-dihydro-6-methoxy-2-(4-methoxyphenyl)-1-naphthalenyl]phenyl] 2-propenamide,
N,N-diethyl 3-[4-[3,4-dihydro-6-hydroxy-2-(4-hydroxyphenyl) 1-naphthalenyl]phenyl] 2-propenamide,
(+,−) cis ethyl 3-[4-[6-methoxy-2-(4-methoxyphenyl) 1,2,3,4-tetrahydro 1-naphthalenyl)phenyl] 2-propenoate,
(+,−) cis ethyl 3-[4-[6-hydroxy-2-(4-hydroxyphenyl) 1,2,3,4-tetrahydro 1-naphthalenyl]phenyl] 2-propenoate,
(+,−) cis 3-[4-[3,4-[6-methoxy-2-(4-methoxyphenyl)] 1,2,3,4-tetrahydro-1-naphthalenyl]phenyl] 2-propenoic acid,
(+,−) cis 3-[4-[6-hydroxy-2-(4-hydroxyphenyl) 1,2,3,4-tetrahydro 1-naphthalenyl]phenyl] 2-propenoic acid,
(+,−) cis N,N-diethyl-3-[4-[6-methoxy-2-(4-methoxyphenyl) 1,2,3,4-tetrahydro 1-naphthalenyl] phenyl] 2-propenamide,
(+,−) cis N,N-diethyl-3-[4-[6-hydroxy-2-(4-hydroxyphenyl) 1,2,3,4-tetrahydro 1-naphthalenyl]phenyl] 2-propenamide,
ethyl 3-[4-[3,4-dihydro-6-methoxy-2-(4-fluorophenyl) 1-naphthalenyl)phenyl] 2-propenoate
ethyl 3-[4-[3,4-dihydro-6-hydroxy-2-(4-fluorophenyl) 1-naphthalenyl)phenyl] 2-propenoate,
3-[4-[3,4-dihydro-6-hydroxy-2-(4-fluorophenyl) 1-naphthalenyl)phenyl] 2-propenoic acid,
3-[4-[6-methoxy-2-(4-fluorophenyl) 3,4-dihydro 1-naphthalenyl]phenyl] 2-propenoic acid,
N,N-diethyl 3-[$^4$-[3,4-dihydro-6-methoxy-2-(4-fluorophenyl) 1-naphthalenyl]phenyl] 2-propenamide,
N,N-diethyl 3-[4-[3,4-dihydro-6-hydroxy-2-(4-fluorophenyl) 1-naphthalenyl]phenyl] 2-propenamide,
(+,−) cis ethyl 3-[4-[6-methoxy-2-(4-fluorophenyl) 1,2,3,4-tetrahydro 1-naphthalenyl]phenyl] 2-propenoate,
(+,−) cis ethyl 3-[4-[6-hydroxy-2-(4-fluorophenyl) 1,2,3,4-tetrahydro 1-naphthalenyl]phenyl] 2-propenoate,
(+,−) cis 3-[4-[2-(4-fluorophenyl) 6-hydroxy 1,2,3,4-tetrahydro 1-naphthalenyl]phenyl] 2-propenoic acid,
(+,−) cis 3-[4-[2-(4-fluorophenyl) 6-methoxy 1,2,3,4-tetrahydro 1-naphthalenyl]phenyl] 2-propenoic acid,
(+,−) cis N,N-diethyl 3-[4-[6-methoxy-2-(4-fluorophenyl) 1,2,3,4-tetrahydro 1-naphthalenyl]phenyl] 2-propenamide,
(+,−) cis N,N-diethyl 3-[4-[6-hydroxy-2-(4-fluorophenyl) 1,2,3,4-tetrahydro 1-naphthalenyl]phenyl] 2-propenamide,
ethyl 3-[4-(3,4-dihydro-6-methoxy-2-phenyl-1-naphthalenyl)phenyl] 2-propenoate,
ethyl 3-[4-(3,4-dihydro-6-hydroxy-2-phenyl-1-naphthalenyl)phenyl] 2-propenoate,
(+,−) cis ethyl 3-[4-(6-methoxy-2-phenyl) 1,2,3,4-tetrahydro-1-naphthalenyl)phenyl] 2-propenoate,
(+,−) cis ethyl 3-[4-(6-hydroxy-2-phenyl-1,2,3,4-tetrahydro-1-naphthalenyl)phenyl] 2-propenoate,
(+,−) cis N,N-diethyl 3-[4-(6-methoxy-2-phenyl-1,2,3,4-tetrahydro 1-naphthalenyl)phenyl] 2-propenamide, these compounds of formula (I) can be in all their possible stereoisomeric forms isolated or in a mixture as well as the addition salts with acids and bases.

A subject of the invention is also a preparation process for the compounds of formula (I) as defined previously, characterized in that a compound of formula (II)

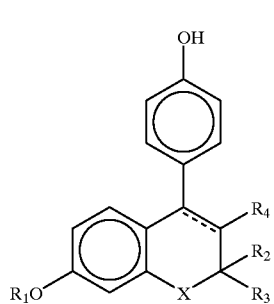

is subjected to the action of a phenol activating agent, then to the action of a compound of formula:

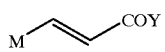

in which M is an organometallic derivative, preferably organostannic, and Y is as defined previously, in order to obtain the compound of formula (I) which if appropriate, if desired or if necessary and in an appropriate order is used in one or more of the following reactions:
alkylation/dealkylation in position 6,
acylation/cleavage of the acyloxy in position 6,
esterification/saponification of the acid or the ester which is represented by COY,
amidification of the acid or the ester which is represented by COY,
salification,
séparation of diastereoisomers, resolution and/or transformation into another isomer.

By phenol activating agent, is meant in particular an agent allowing the formation of the triflate or mesylate, by the action of the corresponding anhydride in basic medium.

The action of the compound of formula (III) on the activated phenol (II) is carried out according to the conditions described by M. R. PEÑA and J. K. STILLE, J. Am. Chem. Soc., 111, (1989), 5417–5424.

The compound of formula (III) is preferably a stannane and the reaction is carried out in the presence of a catalyst such as tetrakis triphenyl phosphine palladium.

The alkylation, dealkylation in position 3, acylation, cleavage of the acyloxy in position 3, esterification, saponification, acidification and salification reactions are carried out according to methods known to a person skilled in the art.

A subject of the invention is also a preparation process for the compounds of formula (I) in which the dotted line represents a double bond, characterized in that a compound of formula (IV):

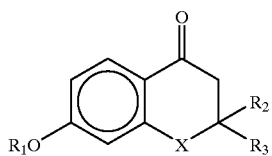

(IV)

R1, R2, R3 and X being as defined previously is subjected to the action of an organo-metallic compound, in particular magnesium or lithium, protected derivative of 4-halogeno benzaldehyde, preferably in the presence of cerium chloride, in order to obtain, after acid treatment, the compound of formula (V):

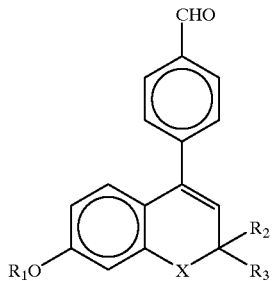

(V)

which compound of formula (V) is subjected to the action of a halogenation reagent in order to obtain a compound of formula (VI):

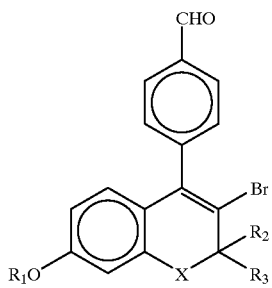

(VI)

which compound of formula (VI) is subjected to the action of an arylation reagent, in order to obtain a compound of formula (VII):

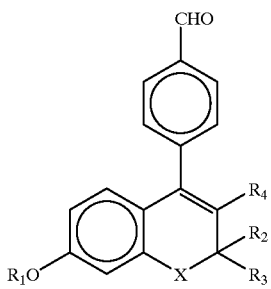

(VII)

which compound of formula (VII) is subjected to the action of a Wittig reagent of formula:

$\phi_3P=CH-COY$ in which Y is as defined previously in order to obtain the compound of formula (I) which, if appropriate, if desired and if necessary and in an appropriate order is used in one or more of the following reactions:

alkylation/dealkylation in position 6, acylation/cleavage of the acyloxy in position 6, esterification/saponification of the acid or ester which is represented by COY, amidification of the acid or ester which is represented by COY, salification, séparation of diastereoisomers, resolution and/or transformation into another isomer.

The action of the protected 4-halogen benzaldehyde, on the compound of formula (IV) is carried out according to the conditions described by T. IMAMOTO et al., J. Am. Chem. Soc., 111, (1989), 4392.

The introduction of a halogen, in particular a bromine in position 2 in order to obtain the compound of formula (VI) is carried out according to the method described in the A preferred method is the action of pyridinium perbromide in tetrahydrofuran.

The substitution reaction of a vinylic halogen by an aryl or a heteroaryl in order to obtain the compound of formula (VII) is carried out according to the method described by T. M. WILSON et al., J. Med. Chem., 37, (1994), 1550.

A preferred method for the introduction of a phenyl consists in the action of phenylboronic acid in the presence of palladium tetrakis triphenyl phosphine and of sodium bicarbonate in a tetrahydrofuran/water medium.

The Wittig reaction is carried out according to standard methods known to a person skilled in the art. Preferably a reagent is used in which Y is an alkyloxy group such as carboethoxymethylenetriphenylphosphorane.

The compounds of general formula (I) as well as their addition salts with pharmaceutically acceptable acids have in particular oestrogen, anti-oestrogen and anti-proliferative activities.

Therefore the compounds of formula (I) can be used in the treatment of disorders linked to hypofolliculinia, for example, amenorrheas, dysmenorrheas, repeated abortions, premenstrual disorders, in the treatment of certain oestrogen-dependent pathologies such as prostatic adenomas or carcinomas, mammary-carcinomas and their metastases or in the treatment of benign breast tumors, as an anti-uterotrophic as well as in the replacement treatment for the menopause or the perimenopause.

Among the symptoms and consequences linked to the menopause are more specifically meant hot flushes, sweats, vaginal atrophy and dryness, urinary symptoms and in the long term a reduction in bone mass and an increased risk of fractures, and the loss of the cardiovascular protection provided by the oestrogens.

In particular, the compounds of formula (I) and their addition salts with pharmaceutically acceptable acids or bases can be used in the prevention or the treatment of osteoporosis.

The compounds of formula (I) and their addition salts with pharmaceutically acceptable acids or bases can also be used for the prevention or the treatment of osteoporosis in man.

They can also be used for the prevention or the treatment of secondary osteoporoses (for example cortisonal, linked with immobilization).

The compounds of formula (I) and their addition salts with pharmaceutically acceptable acids or bases in particular have a dissociated oestrogenic activity.

By dissociated oestrogenic activity is meant an oestrogenic activity at bone level while demonstrating only minimal activity at uterine level, thus not entailing an endometrial proliferation (much lower activity than that of oestradiol).

Furthermore, the compounds according to the invention have the following advantages:

They have an anti-oestrogenic and/or antiproliferative activity at the level of the breast. Unlike oestradiol, they do not stimulate the growth of human mammary tumor cells and can even inhibit their growth. The compounds according to the invention are therefore particularly advantageous for the treatment of the menopause in women at risk from breast cancer (family antecedents) who are therefore excluded from a replacement treatment using oestradiol.

They can also be used in the treatment of breast cancers.

They lead to a lowering of the seric cholesterol level to a level at least equivalent to that induced by oestradiol.

Therefore, they strengthen cardiovascular protection.

Finally, as the compounds according to the invention do not have an oestrogen activity at the uterine level, which does not require them to be administered in combination with a progestomimetic compound.

A subject of the invention is thus compounds of formula (I) as well as their addition salts with pharmaceutically acceptable acids or bases, as medicaments.

A more particular subject of the invention is compounds of formula (I) as defined previously as well as their addition salts with pharmaceutically acceptable acids or bases as medicaments intended for the prevention or the treatment of osteoporosis.

The invention extends to pharmaceutical compositions containing as active ingredient at least one of the medicaments as defined above as well as one or more pharmaceutically acceptable excipients.

The compounds of formula (I) are used by digestive, parenteral or local route, for exempla by percutaneous route. They may be prescribed in the form of plain or coated tablets, capsules, granules, suppositories, pessaries, injectable preparations, ointments, creams, gels, microspheres, implants, intravaginal rings, patches, which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The useful dose varies as a function of the illness to be treated and the administration route; it can vary for example from 1 to 1000 mg per day for an adult by oral route.

The compounds of formula (II) with X=CH2 are described in the Patent U.S. Pat. No. 3,947,520. The compounds of formula (II) with X=O are easily accessible by the method described in this patent.

The compounds of formula (IV) are in the main commercially available or easily accessible to a person skilled in the art.

A subject of the invention is also, as intermediate products, the compounds of formulae (V), (VI) and (VII) as defined previously.

The following examples illustrate the invention without however limiting it.

Solvents described in the examples: AcOEt (ethyl acetate), TEA (triethylamine), CH2Cl2 (dichloromethane), CHCl3 (chloroform), MeOH (methanol), NH4OH (ammonium hydroxide), iPrOH (isopropyl alcohol), EP (petroleum ether).

EXAMPLE 1 ethyl 3-[4-(3,4-dihydro-6-methoxy-2-phenyl-1-naphthalenyl)phenyl]-2-propenoate

Stage A: Introduction of benzaldehyde in position 1: 4-(3,4-dihydro-6-methoxy-1-naphthalenyl)-benzaldehyde 1) Dehydration of CeCl3

10 7.44 g of finely ground CeCl3,7H2O is heated for 2 hours at 140° C. under 10-2 mbar, then returned to ambient temperature under argon then 40 ml of THF/siliporite is introduced and the suspension is agitated for 2 hours at ambient temperature.

2) Preparation of lithium compound 3.66 g of 2-(4-bromophenyl)-1,3-dioxolane is dissolved at ambient temperature under nitrogen, in 36 ml of THF/siliporite, then 10 ml of 1.6M n-butyllithium, is added over 20 minutes at −73° C. ±1° C. and this suspension is agitated for 3 hours 30 minutes at −75° C.

3) Organo-cerium compound

The suspension of CeCl3 is mixed with the suspension of lithium compound and the suspension obtained is agitated for 35 minutes at −70° C.

4) Nucleophilic addition then acid treatment

A solution of 1.408 g of 3,4-dihydro-6-methoxy-1(2H)-naphthalenone in 20 ml of THF is added to the preceding suspension, followed by agitating for 1 hour at −70° C., then 8 ml of HCl is added and agitation is carried out for 1 hour 30 minutes. After filtration, washing and extraction with ethyl acetate, evaporation is carried out under reduced pressure until 3.15 g of expected crude product is obtained which is purified by chromatography eluting with an EP/AcOEt mixture (9/1). 1.78 g of expected pure product is obtained.

Rf EP/AcOEt (9/1)=0.22.

M.P.=100° C.

IR (CHCl3).

C=O 1700 cm$^{-1}$; C=C+aromatic 1604, 1566, 1499 cm$^{-1}$.

Stage B: Bromination: 4-(2-bromo-3,4-dihydro-6-methoxy-1-naphthalenyl)-benzaldehyde 2.15 g of 95% pyridinium perbromide is added to a solution of 1.78 g of the product obtained in the previous stage, in 18 ml of THF, under nitrogen and at ambient temperature, this suspension is agitated for 2 hours 30 minutes at ambient temperature, sodium bicarbonate is added, followed by extraction with ethyl acetate, washing, drying and evaporation under reduced pressure until 3.18 g of expected product is obtained.

Rf EP/AcOEt (9/1)=0.22.

IR (CHCl3).

C=O 1703 cm$^{-1}$, C=C+aromatic 1604 (F), 1569, 1468 cm$^{-1}$.

Stage C: Arylation: 4-(3,4-dihydro-6-methoxy-2-phenyl-1-naphthalenyl)-benzaldehyde The mixture constituted by 3.18 g of the bromination derivative obtained in the previous stage containing ¾ of a mole of HO—(CH2)3-Br, 1.07 g phenylboronic acid, 230 mg of palladium tetrakis triphenyl phosphine, 40 ml of THF, 20 ml of water and 1.82 g of sodium bicarbonate is taken to reflux for 1 hour, followed by decanting, washing, extracting with ethyl acetate, drying and evaporation under reduced pressure until 3.2 g of crude product is obtained which is purified by chromatography eluting with an EP/AcOEt mixture (9/1) in order to obtain 1.92 g of expected crude product.

Rf EP/AcOEt (9/1)=0.23.

M.P.=153° C.

IR (CHCl3).

C=O 1699 cm$^{-1}$; C=C+aromatic 1603, 1567, 1496 cm$^{-1}$.

Stage D: Wittig reaction 1.15 g of carboethoxymethylene triphenylphosphorane is added at ambient temperature and under nitrogen to a solution of 1.02 g of the aldehyde prepared in the previous stage in 10 ml of THF, and this solution is agitated for 5 hours at ambient temperature then for 17 hours under reflux. After evaporation under reduced pressure 2.2 g of crude product is obtained which is purified by chromatography eluting with an EP/AcOEt mixture (8/2). 1.21 g of expected pure product is obtained.

Rf EP/AcOEt (8/2)=0.07.

M.P.=154° C.

IR (CHCl3).

C=O 1705 cm$^{-1}$; C=C 1636 cm$^{-1}$; C=C+aromatic 1605 (max), 1567 (max), 1494 (max); absorption region H—C=C—H trans 1984 cm$^{-1}$.

NMR CDCl3 300 MHz 67 in ppm 2.80 (m) and 2.96 (m): H3 and H4; 1.33 (t) and 4.26 (q): CO2-CH2-CH3; 3.81 (s): OCH3; 7.64 (d,J=16) and 6.39 (d,J=16): Ph—CH=CH—CO2Et; 6.68 (d,J=8.5) H1; 6.59 (dd,J=2.5 and 8.5) H7; 6.79 (d,J=2.5) H3; 6.98 to 7.11 (m): phenyl in position 2; 7.09 and 7.38: phenyl in position 1.

EXAMPLE 2 ethyl 3-[4-(3,4-dihydro-6-hydroxy-2-phenyl-1-naphthalenyl)phenyl]-2-propenoate 1.5 ml of BF3,Me2S is added 4 times to a solution of 776 mg of the compound of Example 1 in 15 ml of dichloromethane, while maintaining at ambient temperature, the reaction medium is poured into salt water, followed by extraction, washing, drying and evaporation under reduced pressure until 800 mg of expected product is obtained.

Rf EP/AcOEt (8/2)=0.15.

EXAMPLE 3

3-[4-(3,4-dihydro-6-hydroxy-2-phenyl-1-naphthalenyl)phenyl]-propenoic acid 4 ml of 2N soda is added to a solution of 800 mg of the ester obtained in Example 2 in 8 ml of methanol, the reaction medium is heated for 15 minutes at 50EC, then returned to ambient temperature, acidified with 2N HCl, followed by extraction with ethyl acetate, washing, drying and evaporation under reduced pressure until 799 mg of crude product is obtained which is purified by chromatography eluting with a CH2Cl2/MeOH mixture (9/1) then by recrystallization from isopropyl ether. 320 mg of expected pure product is obtained.

Rf CH2Cl2/MeOH (90/10)=0.28.

EXAMPLE 4

(+,−) cis ethyl 3-[4-(6-methoxy-2-phenyl-1,2,3,4-tetrahydro-1-naphthalenyl)phenyl]-2-propenoate Stage A: hydrogenation: (+,−) cis 4-(6-methoxy-2-phenyl-1,2,3,4-tetrahydro-1-naphthalenyl)-phenol 30 mg of palladium on carbon at 9.5% is added to a solution of 268 mg of 4-(3,4-dihydro-6-methoxy-2-phenyl-1-naphthalenyl)-phenol (prepared according to U.S. Pat. No. 3,947,520) in 2 ml of ethanol and 2 ml of acetic acid, then hydrogenation is carried out at a temperature of 55° C., for 24 hours (3.5 bars). After treatment, 235 mg of expected product is obtained.

Rf MeOH/H2O (9/1)=0.25 (Whatman KCl8).

M.P.=187° C.

Stage B: Activation of phenol: (+,−) cis 4-(6-methoxy-2-phenyl-1,2,3,4-tetrahydro-1-naphthalenyl)-phenyl trifluoromethane sulphonate 1.35 ml triflic anhydride is added dropwise, using a water bath, to a solution of 1.77 g of the product obtained in the previous stage in 30 ml of pyridine and agitation is carried out for 50 minutes while leaving the reaction medium to return to ambient temperature. After dilution with ethyl acetate, washing with 2N hydrochloric acid, with sodium bicarbonate then with water, and drying, evaporation is carried out under reduced pressure in order to obtain 2.53 g of crude product which is purified by chromatography eluting with an EP/AcOEt mixture (95/5).

Rf EP/AcOEt (95/5)=0.26.

M.P.=130° C.

IR (CHCl3).

Absence of OH.

Aromatic 1610–1499 cm$^{-1}$.

Stage C: Coupling with the stannane

The mixture constituted by 2.15 g of (E) ethyl 3-(tributylstannyl)-2-propenoate (prepared according to J.A.C.S. (1987) 109 815)

1262 mg of the triflate prepared in the previous stage 12 ml of DMF 164 mg of Pd(Pφ3)4

349 mg of lithium chloride, is heated under nitrogen for 15 minutes at 100EC followed by pouring into water, extracting with ethyl acetate, washing, drying and evaporation under reduced pressure until 3.7 g of crude product is obtained. After redissolving in ethyl acetate, potassium fluoride is added, followed by drying, evaporation under reduced pressure and purification by chromatography eluting with an EP/AcOEt mixture (9/1) then with a CH3CN/H2O mixture (9/1) (Lichrosort RP18).

613 mg of expected pure product is obtained.

Rf CH3CNH2O (9/1)=0.3.

NMR: CDCl3, 300 MHz, 67 in ppm 1.31 (t) and 4.23 (q): CO2-CH2-CH3; 1.86 (dm) and 2.18 (m): H3; 3.00 to 3.20 (m): H4; 3.43 (ddd,J=3.5 and 13): H2; 4.31 (d,J=5): H1; 3.82 (s): OCH3; 7.56 (d,J=16) and 6.30 (d,J=16): Ph—CH=CH—CO2Et; 6.44 and 7.15: phenyl in position 1; 6.68 (dd): H7; 6.78 (d): H5; 6.84 (d): H8; 6.80 (m) and 7.15 (m): phenyl in position 2.

EXAMPLE 5

(+,−) cis ethyl 3-[4-(6-hydroxy-2-phenyl-1,2,3,4-tetrahydro-1-naphthalenyl)phenyl]-2-propenoate The operation is carried out as in Example 2 but starting with 300 mg of the product of Example 4. 300 mg of expected demethoxylated product is obtained.

Rf EP/AcOEt (80/20)=0.15.

EXAMPLE 6

(+,−) cis 3-[4-(6-hydroxy-2-phenyl-1,2,3,4-tetrahydro-1-naphthalenyl)phenyl]-propenoic acid The operation is carried out as in Example 3, but starting with 300 mg of the product of Example 5.

235 mg of expected saponified product is obtained.

Rf CH2Cl2/MeOH (9/1)=0.3.

NMR CDCl3+C5D5N−300 MHz, 67 in ppm 1.75 and 2.11: H3; 2.99 (m): H4; 3.38 (dm): H2; 4.30 (d,J=5): H1; 7.40 (d,J=16) and 6.36 (d,J=16): Ph—CH=CH—CO2Et; 6.41 and 7.26: phenyl in position 1; 6.50 (dd): H7; 6.65: H5 and H8; 6.86 and 7.13: phenyl in position 2.

EXAMPLE 7

(+,−) cis N,N-diethyl-3-[4-(6-methoxy-2-phenyl-1,2,3,4-tetrahydro-1-naphthalenyl)phenyl]-2-propenamide Stage A: (+,−) cis 3-[4-(6-methoxy-2-phenyl-1,2,3,4-tetrahydro-1-naphthalenyl)phenyl]-2-propenoic acid The operation is carried out as in Example 3, but starting with 304 mg of the ester of Example 4. 300 mg of expected product is obtained.

Rf CH2Cl2/MeOH (90/10)=0.4.

NMR (DMSO), 300 MHz, 67 in ppm 1.78 (m) and 2.13 (m): H3; 2.90 to 3.15 (m): H4; 3.40 (m): H2; 4.35 (d,J=5): H1; 7.42 (d,J=16) and 6.36 (d,J=16): Ph—CH=CH—COO; 6.42 and 7.29: phenyl in position 1; 6.66 (dd): H7; 6.77 (d): H8; 6.82 (d): H5; 6.87 (m) and 7.15 (m): phenyl in position 2.

Stage B: (+,−) cis N,N-diethyl-3-[4-(6-methoxy-2-phenyl-1,2,3,4-tetrahydro-1-naphthalenyl)phenyl]-2-propenamide 180 μl of methylmorpholine, then, at about −10° C., 150 μl of isobutyl chloroformate then 320 μl of diethylamine are added, at ambient temperature and under nitrogen, to a solution of 296 mg of the acid obtained in the previous stage in 5 ml of dichloromethane. After agitation for 30 minutes at −10° C., ethyl acetate is added, followed by washing with 2N hydrochloric acid, with sodium bicarbonate and with salt water, drying and evaporation under reduced pressure until 380 mg of expected product is obtained.

Rf EP/acetone (50/50)=0.6.

EXAMPLE 8

(+,−) cis N,N-diethyl-3-[4-(6-hydroxy-2-phenyl-1,2,3,4-tetrahydro-1-naphthalenyl)phenyl]-2-propenamide The operation is carried out as in Example 2 but starting with 380 mg of the amide prepared according to Example 7. 240 mg of expected pure product is obtained.

Rf EP/acetone (6/4)=0.35.

M.P.=222° C.

IR (Nujol).

Absorption region OH/NH.

C=O 1637 cm$^{-1}$; conjugated system+aromatic 1574, 1505, 1499 cm$^{-1}$.

NMR (DMSO) 300 MHz 1.04 (t) and 1.10 (t); 3.30 to 3.50 (m): CONEt2; 1.75 (dm) and 2.11 (m) H4; 2.88 to 3.10 (m) H3; 3.40 masked H2; 4.29 (d,J=5.5) H1; 7.33 (d,J=15.5), 6.92 (d,J=15.5): Ph—CH=CH—CO; 6.40 to 7.30 phenyl in position 1; 6.50 (dd) 1H, 6.65 (m) 2H, 6.87 (m) 2H, 7.14 (m) aromatic 3H's.

EXAMPLE 9 ethyl 3-[4-[3,4-dihydro-6-methoxy-2-(4-methoxyphenyl)-1-naphthalenyl]phenyl] 2-propenoate Stage A: Arylation: 4-[3,4-dihydro-6-methoxy-2-(4-methoxyphenyl) 1-naphthalenyl]phenol The mixture constituted by 10.2 g of 4-(2-bromo 3,4-dihydro 6-methoxy 1-naphthalenyl)phenol, 4.9 g of 4-methoxy benzene boronic acid, 820 mg of palladium tetrakistriphenylphosphine, 100 ml of tetrahydrofuran, 50 ml of water and 7.3 g of sodium carbonate is heated for 1 hour under reflux followed by decanting, washing, extracting with ethyl acetate, drying and evaporation under reduced pressure until 12.65 g of crude product is obtained which is purified by chromatography eluting with an EP-AcOEt mixture (7-3) in order to obtain 8 g of expected crude product.

Rf: EP-AcOEt 9-1=0.23.

M.P.=180° C.

IR (CHCl3): OH 3598 cm$^{-1}$; OMe 2837 cm$^{-1}$; C=C+aromatic 1608, 1568, 1494 cm$^{-1}$.

Stage B: Activation of phenol: 4-(6-methoxy 2-(4-methoxyphenyl) 3,4-dihydro 1-naphthalenyl)phenyl trifluoromethane sulphonate The operation is carried out as in Stage B of Example 4 using 1.79 g of the product obtained in Stage A, 18 ml of pyridine and 1.25 ml of triflic anhydride. 2.26 g of expected product is obtained. M.P.=130° C.

IR (CHCl3).

Absence of OH; C=C+aromatic 1608, 1566, 1511, 1498 cm$^{-1}$; OSO2CF3 1423, 1141 cm$^{-1}$.

Stage C: Coupling with the stannane: ethyl 3-[4-[3,4-dihydro-6-methoxy-2-(4-methoxyphenyl)-naphthalenyl]phenyl] 2-propenoate The operation is carried out as in Stage C of Example 4 using 2.25 g of (E) ethyl 3-(tributylstannyl) 2-propenoate [prepared according to J.A.C.S. (1987) 109, 815], 2.69 g of the triflate prepared in the previous stage, 25 ml of dimethylformamide, 275 mg of Pd(Pϕ3)4 and 588 mg of lithium chloride. 1.4 g of expected product is obtained.

M.P.=145° C.

Rf: 0.23 (EP-AcOEt 85-15).

IR (CHCl3).

C=O 1705 cm$^{-1}$; C=C 1636 cm$^{-1}$; aromatic 1608, 1568, 1511, 1496 cm$^{-1}$.

EXAMPLE 10 ethyl 3-[4-[3,4-dihydro-6-hydroxy-2-(4-hydroxyphenyl)-1-naphthalenyl]phenyl] 2-propenoate.

The operation is carried out as in Example 2 using 948 mg of the product obtained in Example 9 and 4.2 ml of BF3, Me2S. 785 mg of crude product is obtained which is chromatographed on silica eluting with an EP-AcOEt mixture 1-1 and 600 mg of pure product is recovered. M.P.=214° C.

Rf=0.37 (EP-AcOEt 1-1).

EXAMPLE 11

3-[4-[3,4-dihydro-6-hydroxy-2-(4-hydroxyphenyl) 1-naphthalenyl]phenyl] 2-propenoic acid The operation is carried out as in Example 3 using at the start 365 mg of the ester prepared in Example 10. 326 mg of pure product is obtained. M.P.=180° C.

Rf=0.3 (CH2Cl2-MeOH 85-15).

EXAMPLE 12

3-[4-[6-methoxy-2-(4-methoxyphenyl)-3,4dihydro 1-naphthalenyl]phenyl] 2-propenoic acid The operation is carried out as in Example 7A using 440 mg of the ester prepared in Example 9. 406 mg of expected product is obtained. M.P.≈206° C.

EXAMPLE 13

N,N-diethyl 3-[4-[3,4-dihydro-6-methoxy-2-(4-methoxyphenyl) 1-naphthalenyl]phenyl] 2-propenamide The operation is carried out as in Example 7B using 400 mg of the acid prepared in Example 12, 0.23 ml of methylmorpholine, 0.2 ml of isobutyl chloroformate and 0.42 ml of diethylamine. 557 mg of expected product is obtained which is used as it is for the following example.

EXAMPLE 14

N,N-diethyl 3-[4-[3,4-dihydro-6-hydroxy-2-(4-hydroxyphenyl) 1-naphthalenyl]phenyl] 2-propenamide The operation is carried out as in Example 8 using 557 mg of the compound prepared in Example 13 and 2.1 ml of $BF_3,Me_2S$ and 335 mg of expected product is obtained.

M.P.=222° C.

Rf=0.32 (EP-acetone 1-1).

NMR (CDCl3) 200 MHz 1.19 (t) −1.26 (t) −3.49 (m): CONEt2; 2.75 (m) 2H and 2.92 (m) 2H: H3 and H4; 4.98 (wide s): the OH's; 6.60 and 6.88: phenyl in position 2; 6.79 (d,J=15.5) −7.67 (d,J=15.5): Ph—CH=CH—CO; 7.06 and 7.37: phenyl in position 1.

EXAMPLE 15

(+,−) cis ethyl 3-[4-[6-methoxy-2-(4-methoxyphenyl) 1,2,3,4-tetrahydro 1-naphthalenyl] phenyl] 2-propenoate By operating as in Example 4, Stages A, B, C starting with the phenol prepared in Example 9, Stage A, the expected product was prepared.

Rf: 0.24 (EP-AcOEt 85-15).

IR (CHCl3).

OMe 2838 $cm^{-1}$; C=O 1704 $cm^{-1}$; C=C conj. 1636 $cm^{-1}$; aromatics 1609 (F), 1513 (F), 1501 (F) $cm^{-1}$; C=C ΔE 984 $cm^{-1}$.

EXAMPLE 16

(+,−) cis ethyl 3-[4-[6-hydroxy-2-(4-hydroxyphenyl) 1,2,3,4-tetrahydro 1-naphthalenyl] phenyl] 2-propenoate The operation is carried out as in Example 2 using 313 mg of the product obtained in Example 15 and 1.4 ml of $BF_3,Me_2S$. 299 mg of crude product is obtained which is chromatographed on silica (eluant EP-AcOEt 6-4) and 244 mg of pure product is recovered.

Rf=0.30 (EP-AcOEt 6-4).

IR (Nujol).

OH 3418 $cm^{-1}$; C=O 1685 $cm^{-1}$; aromatic 1620, 1612, 1587, 1514 (F) 1493 $cm^{-1}$; C=C ΔE def. 980 $cm^{-1}$.

EXAMPLE 17

(+,−) cis 3-[4-[6-methoxy-2-(4-methoxyphenyl) 1,2,3,4-tetrahydro 1-naphthalenyl]phenyl] 2-propenoic acid.

The operation is carried out as in Example 3, but starting with 1.3 g of the ester of Example 15. 1.2 g of expected product is obtained. Rf=0,4 (CH2Cl2-MeOH 90-10).

NMR (DMSO), 300 MHz, Δ in ppm 1.82 (dl) and 2.12 (m): H3; ●3.10 (ml): H4; 3.38 (ddd): H2; 4.28 (d, J=5): H1; 7.66 (d, J=16) and 6.30 (d, J=16): Ph—CH=CH—COO; 6.47 and 7.18: phenyl in position 1; 6.68: H7; 6.89 (d, J=9): H8; 6.78 (d, J=2): H5; 6.72: phenyl in position 2.

EXAMPLE 18

(+,−) cis 3-[4-[6-hydroxy-2-(4-hydroxyphenyl) 1,2,3,4-tetrahydro 1-naphthalenyl]phenyl] 2-propenoic.

270 mg of the acid prepared in Example 17 is heated at 160° C. for 4.5 hours in the presence of 3 g of pyridine hydrochloride. The reaction medium is left to return to ambient temperature, followed by extracting with ethyl acetate, washing with 2N hydrochloric acid, then with water and concentrated. 309 mg of crude product is obtained which is chromatographed on silica (eluant: CH2Cl2-MeOH 85-15) and 177 mg of expected product is obtained.

Rf=0.3 (CH2Cl2-MeOH 85-15).

IR (Nujol).

General absorption: OH/NH; C=O: 1622 $cm^{-1}$; C=C+aromatic: 1629, 1605, 1560, 1513, 1499 $cm^{-1}$.

EXAMPLE 19

(+,−) cis N,N-diethyl 3-[4-[6-methoxy-2-(4-methoxyphenyl) 1,2,3,4-tetrahydro 1-naphthalenyl] phenyl] 2-propenamide.

The operation is carried out as in Example 7B using 300 mg of the acid prepared in Example 17, 0.16 ml of methylmorpholine, 0.14 ml of isobutyl chloroformate and 0.22 ml of diethylamine. 425 mg of expected product is obtained which is used as it is for the following example.

EXAMPLE 20

(+,−) cis N,N-diethyl 3-[4-[6-hydroxy-2-(4-hydroxyphenyl) 1,2,3,4-tetrahydro 1-naphthalenyl] phenyl] 2-propenamide.

The operation is carried out as in Example 8 using 425 mg of the compound prepared in Example 19 and 1.4 ml of $BF_3,Me_2S$ and 202 mg of expected product is obtained.

Rf=0.30 (EP-acetone 1-1).

NMR (DMSO), 300 MHz Δ in ppm 1.05 (t) −1.11 (t) −≈3.32 (m) −3.46 (m): CONEt2; 1.69 (m) and 2.02 (m): H3; 2.97 (m): H4; 3.26 (m): H2; 4.21 (d, J=5): H1;

7.34 (d, J=15.5) and 6.93 (d, J=15.5): Ph—CH=CH—; 6.41 and 7.31, 6.54 and 6.63: the phenyls in positions 1 and 2; 6.48 (dd): H7; 6.60 to 6,.69: H5.

By operating as in the previous examples, the products of the following examples were prepared:

EXAMPLE 21 ethyl 3-[4-[3,4-dihydro 6-methoxy-2-(4-fluoro-phenyl) 1-naphthalenyl]phenyl] 2-propenoate Stage A: Arylation: 4-[3,4-dihydro 6-methoxy-2-(4-fluoro-phenyl) 1-naphthalenyl]phenol

M.P.=142° C.

Rf=0.26 (EP-AcOEt 8-2).

IR (CHCl3).

OH: 3596 $cm^{-1}$; C=C+aromatic: 1605, 1591, 1568, 1507, 1495 $cm^{-1}$.

Stage B: Activation of phenol: 4-[6-methoxy-2-(4-fluoro-phenyl) 3,4-dihydro 1-naphthalenyl]phenyl trifluoromethane sulphonate Rf=0.35 (Ep-AcOEt 9-1).

IR (CHCl3).
C=C+aromatic: 1606, 1568, 1508, 1499 cm$^{-1}$; OSO2CF3: 1424 and 1141 cm$^{-1}$.

Stage C: Coupling with the Stannane: ethyl 3-[4-[3,4-dihydro 6-methoxy-2-(4-fluorophenyl) 1-naphthalenyl] phenyl] 2-propenoate Rf=0.3 (cyclohexane-AcOEt 85-15).
IR (CHCl3).
C=O: 1705 cm$^{-11}$ conjugated ester; C=C: 1637 cm$^{-1}$; aromatic: 1606, 1569, 1508, 1497 cm$^{-1}$.

EXAMPLE 22 ethyl 3-[4-[3,4-dihydro 6-hydroxy-2-(4-fluorophenyl) 1-naphthalenyl]phenyl] 2-propenoate M.P.=196° C.
Rf=0.27 (EP-AcOEt 7-3).
IR (CHCl3).
OH: 3595 cm$^{-1}$; C=O: 1706 cm$^{-1}$; C=C: 1637 cm$^{-1}$; aromatic: 1605, 1590, 1575, 1558, 1508, 1497 cm$^{-1}$.

EXAMPLE 23

3-[4-[3,4-dihydro 6-hydroxy-2-(4-fluorophenyl) 1-naphthalenyl]phenyl]-propenoic acid Rf=0.25 (CH2Cl2-MeOH 9-1).
IR (Nujol).
C=O: 1684 cm$^{-1}$; C=C: 1629 cm$^{-1}$; aromatic: 1603, 1574, 1505 cm$^{-1}$.

EXAMPLE 24

3-[4-[6-methoxy-2-(4-fluorophenyl) 3,4-dihydro 1-naphthalenyl]phenyl] 2-propenoic acid Rf=0.37 (CHCl2-MeOH 9-1).
NMR (DMSO), 300 MHz ppm 3.75 (s): MeO; ≈2.70≈2.93: H3 and H4; 6.49 (d, J=15.5) and 7.55 (d, J=15.5): φ—CH2=CH2-CO.

EXAMPLE 25

N,N-diethyl 3-[4-[3,4-dihydro 6-methoxy-2-(4-fluorophenyl) 1-naphthalenyl]phenyl] 2-propenamide

EXAMPLE 26

N,N-diethyl 3-[4-[3,4-dihydro 6-hydroxy-2-(4-fluorophenyl) 1-naphthalenyl]phenyl] 2-propenamide M.P. ≈240° C.
Rf=0.33 (EP-Acetone 6-4).
IR (Nujol) general absorption: OH/NH; C=O: 1640 cm$^{-1}$; C=C+aromatic: 1605, 1574, 1502, 1484 cm$^{-1}$.

EXAMPLE 27

(+,-) cis ethyl 3-[4-[6-methoxy-2-(4-fluoro-phenyl) 1,2,3,4-tetrahydro 1-naphthalenyl]phenyl] 2-propenoate Rf=0.27 (cyclohexane-AcOEt 9-1).
IR (CHCl3).
C=O: 1705 cm$^{-1}$; C=C: 1637 cm$^{-1}$; aromatic: 1608, 1578, 1565, 1510, 1501 cm$^{1}$.

EXAMPLE 28

(+,-) cis ethyl 3-[4-[6-hydroxy-2-(4-fluoro-phenyl) 1,2,3,4-tetrahydro 1-naphthalenyl]phenyl] 2-propenoate Rf=0.28 (EP-AcOEt 7-3).
IR (CHCl3).
OH: 3599 cm$^{-1}$; C=O: 1703 cm$^{-1}$; C=C: 1637 cm$^{-1}$; aromatic: 1607, 1585, 1565, 1510, 1499 cm$^{-1}$.

EXAMPLE 29

(+,-) cis 3-[4-[2-(4-fluorophenyl) 6-hydroxy 1,2,3,4-tetrahydro 1-naphthalenyl]phenyl] 2-propenoic acid Rf=0.28 (CH2Cl2-MeOH 9-1).
IR (Nujol) absorption region: OH/NH; C=O: 1682 cm$^{-1}$; C=C+aromatic: 1626, 1600, 1560, 1500 cm$^{-1}$.

EXAMPLE 30

(+,-) cis 3-[4-[2-(4-fluorophenyl) 6-methoxy 1,2,3,4-tetrahydro 1-naphthalenyl]phenyl] 2-propenoic acid Rf=0.4 (CH2Cl2-MeOH 9-1).
IR (CHCl3) acid absorption OH type; C=O: 1688 cm$^{-1}$; C=C: 1630 cm$^{-1}$; aromatic: 1607, 1576 (f), 1563 (f), 1510, 1501 cm$^{-1}$.

EXAMPLE 31

(+,-) cis N,N-diethyl 3-[4-[6-methoxy-2-(4-fluorophenyl) 1,2,3,4-tetrahydro 1-naphthalenyl] phenyl] 2-propenamide Rf=0.48 (EP-Acetone 6-4).

EXAMPLE 32

(+,-) cis N,N-diethyl 3-[4-[6-hydroxy-2-(4-fluorophenyl) 1,2,3,4-tetrahydro 1-naphthalenyl] phenyl] 2-propenamide M.P.=260° C.
Rf=0.32 (EP-Acetone 6-4).
IR (Nujol) general absorption: OH/NH; C=O: 1640 cm$^{-1}$; C=C+aromatic: 1600, 1580, 1508, 1498 cm$^{-1}$.

Pharmacological tests

1—Effect on the proliferation of mammary cells

The proliferative activity of the molecules is studied in comparison to that of oestradiol on MCF-7 human mammary cells in culture.

In order to reveal an agonist effect of the oestradiol and/or the tested molecules, the cell maintenance culture (rich in growth factors and steroids) is replaced by an impoverished medium, amongst others free of steroids (DMEM supplemented with 5% of steroid-free serum and without phenol red). Cells undergo this severance two days before the start of the test.

After 7 days culture in the presence of the products to be studied, the cell proliferation is evaluated by determination of the DNA. In each test, the effect of the oestradiol at 10-10M (cell growth in the presence of oestradiol less cell growth in the presence of the solvent) determines the 100% agonist activity. The activity of the molecules is evaluated in comparison to this internal control. The molecules inducing an identical cell growth to that observed with the solvent alone are classified as "inactive", those inducing a lower cell growth to that observed with the solvent are classified as "inhibitor".

| Oestradiol | ACTIVITY |
|---|---|
| Example 3 | Inhibitor |
| Example 6 | Inhibitor |
| Example 8 | Inhibitor |

Conclusion:

The products tested are not agonists of the growth of MCF-7 cells, certain of them are even inhibitors of it.

2—Affinity for the human oestrogen receptor (HOR)

A cytosolic extract of SF9 cells containing the recombinant human oestrogen receptor is obtained by overexpression in an insect-Baculovirus cell system, according to the general methodology described by N. R. WEBB et al. (Journal of Methods in Cell and Molecular Biology, (1990) vol 2 nE 4, 173–188) and the application of which is described for the expression of human hormonal receptors, for example the human glucocorticoid receptor (G. SRINIVASAN et al. Molecular Endocrinology (1990) vol 4 nE 2 209–216).

The BaculoGold Transfection Kit (PharMingen, reference 21000K) is used to generate the recombinant baculovirus containing the fragment of cDNA described in the expression vector HEGO by L. TORA et al. (The EMBO Journal (1989) vol 8 nE 7 1981–1986), containing the region coding for the human oestrogen receptor of wild type with a glycine in position 400.

The recombinant virus thus obtained is used to express the progestogen receptor in the SF9 insect cells (ATCC CRL1711), according to the known methodology mentioned previously.

$2 \times 10^7$ SF9 cells are cultured in a 175 cm2 "Falcon" flask in a TNM-FH "SIGMA" medium supplemented with 10% foetal calf serum (FCS) and with 50 micrograms/ml of gentamycin. After infection then incubation at 27EC for 40 to 42 hours, the cells are lysed in 1 ml of lysis buffer (Tris 20 mM-HCl pH8, EDTA 0.5 mM, DTT 2 mM, Glycerol 20%, KCl 400 mM) with a freezing-thawing cycle which is repeated twice more. The supernatant, containing the recombinant human oestrogen receptor is preserved in liquid nitrogen by 0.5 ml dose.

The supernatant is incubated at OEC for 24 hours with a constant concentration (T) of tritiated oestradiol in the presence of increasing concentrations either of unlabelled oestradiol ($0-1000 \times 10^{-9}$M), or of unlabelled product to be tested ($0-25000 \times 10^{-9}$M). The concentration of bound tritiated oestradiol (B) is then measured in each incubate using the carbon dextran adsorption technique.

3—Calculation of the relative bond affinity (RBA)

The following two curves are drawn: the percentage of bound tritiated hormone 100×B/BO as a function of the logarithm of the concentration of unlabelled reference hormone or as a function of the logarithm of the concentration of unlabelled test product.

The straight line of the following equation $$I50=100(B0/B0+Bmin/B0)/2=100(1+Bmin/B0)=50(1+Bmin/B0)$$

is determined.

B0=Concentration of bound tritiated hormone in the absence of any unlabelled product, B=Concentration of bound tritiated hormone in the presence of a concentration X of unlabelled product, Bmin=Concentration of bound tritiated hormone for an incubation of this tritiated hormone at a concentration (T) in the presence of a large excess of unlabelled reference hormone ($10000 \times 10^{-9}$M) for human receptor.

The intersections of the straight line I50 and the curves allow the evaluation of the concentrations of unlabelled reference hormone (CH) and of the unlabelled test product (CX) which inhibit by 50% the binding of the tritiated hormone on the receptor.

The relative bond affinity (RBA) of the test product is calculated by the equation:

$$RBA=100 \; (CH)/(CX)$$

The results obtained are as follows:

| EXAMPLES | EH oestradiol = 100<br>24 H |
|---|---|
| 3 | 72 |
| 6 | 39 |
| 8 | 5 |

Conclusion:

The products tested have a good affinity for the human oestrogen receptor.

What I claim is:

1. A compound selected from the group consisting of all possible stereoisomeric forms and mixtures thereof of a compound of the formula

I wherein $R_1$ is selected from the group consisting of hydrogen, alkyl of 1 to 6 carbon atoms and acyl of an organic carboxylic acid of 2 to 6 carbon atoms, $R_2$ and $R_3$ are individually hydrogen or alkyl of 1 to 6 carbon atoms or together with the carbon atom to which they are attached form cycloalkyl of 3 to 7 carbon atoms, $R_4$ is aryl or heteroaryl, X is —O— or —$CH_2$—, Y is selected from the group consisting of —OH, alkoxy of 1 to 6 carbon atoms and $$-N\begin{matrix}R_a\\R_b\end{matrix},$$

$R_a$ and $R_b$ are individually hydrogen or alkyl of 1 to 6 carbon atoms or together with nitrogen to which they are attached form a mono- or polycyclic heterocycle of 3 to 15 ring members optionally containing at least one heteroatom selected from the group consisting of oxygen, sulfur and nitrogen, the dotted line is an optional double bond and their salts with non-toxic, pharmaceutically acceptable acids and bases, the said alkyl, acyl aryl and heteroaryl optionally substituted with at least one member of the group consisting of halogen, alkoxy of 1 to 6 carbon atoms, alkylthio of 1 to 6 carbon atoms, amino, mono- and dialkylamino of 1 to 6 alkyl carbon atoms, —OH, acyloxy of an organic carboxylic acid of 2 to 6 carbon atoms, carboxy, carboxy esterified with an alkanol of 1 to 6 carbon atoms, salified carboxy, —CF, —CN, aryl and aralkyl.

2. A compound of claim 1 wherein $R_1$, $R_2$ and $R_3$ are hydrogen, $R_4$ is optionally substituted phenyl and Y is selected from the group consisting of —OH, alkoxy of 1 to 6 carbon atoms and

and $R_a$ and $R_b$ are individually hydrogen or alkyl of 1 to 6 carbon atoms.

3. A compound of claim 1 wherein $R_4$ and

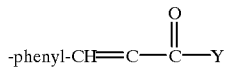

are in cis position.

4. A compound of claim 1 selected from the group consisting of
3-[4-(3,4-dihydro-6-hydroxy-2-phenyl-1-naphthalenyl) phenyl] 2-propenoic acid,
(+,–) cis 3-[4-(6-hydroxy-2-phenyl-1,2,3,4-tetrahyro-1-naphthalenyl)phenyl] 2-propenoic acid,
(+,–) cis N,N-diethyl-3-[4-(6-hydroxy-2-phenyl-1,2,3,4-tetrahydro-1-naphthalenyl)phenyl] 2-propenamide,
ethyl 3-[4-(3,4-dihydro-6-methoxy-2-(4-methoxyphenyl)-naphthalenyl)phenyl] 2-propenoate,
ethyl 3-4-(3,4-dihydro-6-hydroxy-2-(4-hydroxyphenyl) 1-naphthalenyl)phenyl] 2-propenoate,
3-[4-(3,4-dihydro-6-hydroxy-2-(4-hydroxyphenyl)-naphthalenyl)phenyl] 2-propenoic acid,
3-[4-(6-methoxy-2-(4-methoxyphenyl) 3,4-dihydro 1-naphthalenyl)phenyl] 2-propenoic acid,
N,N-diethyl 3-[4-[3,4-dihydro-6-methoxy-2-(4-methoxyphenyl) 1-naphthalenyl]phenyl] 2-propenamide,
N,N-diethyl 3-[4-[3,4-dihydro-6-hydroxy-2-(4-hydroxyphenyl) 1-naphthalenyl]phenyl] 2-propenamide,
(+,–) cis ethyl 3-[4-[6-methoxy-2-(4-methoxyphenyl) 1,2,3,4-tetrahydro 1-naphthalenyl)phenyl] 2-propenoate,
(+,–) cis ethyl 3-[4-[6-hydroxy-2-(4-hydroxyphenyl) 1,2,3,4-tetrahydro 1-naphthalenyl]phenyl] 2-propenoate,
(+,–) cis 3-[4-[3,4-[6-methoxy-2-(4-methoxyphenyl)]1,2,3,4-tetrahydro-1-naphthalenyl]phenyl] 2-propenoic acid,
(+,–) cis 3-[4-[6-hydroxy-2-(4-hydroxyphenyl) 1,2,3,4-tetrahydro 1-naphthalenyl]phenyl] 2-propenoic acid,
(+,–) cis N,N-diethyl-3-[4-[6-methoxy-2-(4-methoxyphenyl) 1,2,3,4-tetrahydro 1-naphthalenyl] phenyl] 2-propenamide,
(+,–) cis N,N-diethyl-3-[4-[6-hydroxy-2-(4-hydroxyphenyl) 1,2,3,4-tetrahydro 1-naphthalenyl]phenyl] 2-propenamide,
ethyl 3-[4-[3,4-dihydro-6-methoxy-2-(4-fluorophenyl) 1-naphthalenyl)phenyl] 2-propenoate,
ethyl 3-[4-[3,4-dihydro-6-hydroxy-2-(4-fluorophenyl) 1-naphthalenyl)phenyl] 2-propenoate,
3-[4-[3,4-dihydro-6-hydroxy-2-(4-fluorophenyl) 1-naphthalenyl)phenyl] 2-propenoic acid,
3-[4-[6-methoxy-2-(4-fluorophenyl) 3,4-dihydro 1-naphthalenyl]phenyl] 2-propenoic acid,
N,N-diethyl 3-[4-[3,4-dihydro-6-methoxy-2-(4-fluorophenyl) 1-naphthalenyl]phenyl] 2-propenamide,
N,N-diethyl 3-[4-[3,4-dihydro-6-hydroxy-2-(4-fluorophenyl) 1-naphthalenyl]phenyl] 2-propenamide,
(+,–) cis ethyl 3-[4-[6-methoxy-2-(4-fluorophenyl) 1,2,3,4-tetrahydro 1-naphthalenyl]phenyl] 2-propenoate,
(+,–) cis ethyl 3-[4-[6-hydroxy-2-(4-fluorophenyl) 1,2,3,4-tetrahydro 1-naphthalenyl]phenyl] 2-propenoate,
(+,–) cis 3-[4-[2-(4-fluorophenyl) 6-hydroxy-1,2,3,4-tetrahydro 1-naphthalenyl]phenyl] 2-propenoic acid,
(+,–) cis 3-[4-[2-(4-fluorophenyl) 6-methoxy 1,2,3,4-tetrahydro 1-naphthalenyl]phenyl] 2-propenoic acid,
(+,–) cis N,N-diethyl 3-[4-[6-methoxy-2-(4-fluorophenyl) 1,2,3,4-tetrahydro 1-naphthalenyl]phenyl] 2-propenamide,
(+,–) cis N,N-diethyl 3-[4-[6-hydroxy-2-(4-fluorophenyl) 1,2,3,4-tetrahydro 1-naphthalenyl]phenyl] 2-propenamide,
ethyl 3-[4-(3,4-dihydro-6-methoxy-2-phenyl-1-naphthalenyl)phenyl] 2-propenoate,
ethyl 3-[4-(3,4-dihydro-6-hydroxy-2-phenyl-1-naphthalenyl)phenyl] 2-propenoate,
(+,–) cis ethyl 3-[4-(6-methoxy-2-phenyl) 1,2,3,4-tetrahydro-1-naphthalenyl)phenyl] 2-propenoate,
(+,–) cis ethyl 3-[4-(6-hydroxy-2-phenyl-1,2,3,4-tetrahydro-1-naphthalenyl)phenyl] 2-propenoate, and
(+,–) cis N,N-diethyl 3-[4-(6-methoxy-2-phenyl-1,2,3,4-tetrahydro 1-naphthalenyl)phenyl] 2-propenamide.

5. A method of treating osteoporosis in warm-blooded animals comprising administering to warm-blooded animals an effective amount of a compound of claim 1 to treat osteoporosis.

6. The method of claim 5 wherein $R_1$, $R_2$ and $R_3$ are hydrogen, $R_4$ is optionally substituted phenyl and Y is selected from the group consisting of —OH, alkoxy of 1 to 6 carbon atoms and

and $R_a$ and $R_b$ are individually hydrogen or alkyl of 1 to 6 carbon atoms.

7. The method of claim 5 wherein $R_4$ and

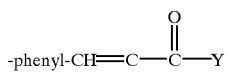

are in cis position.

8. A compound of a formula selected from the group consisting of

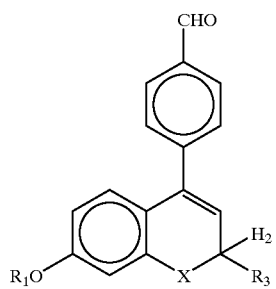

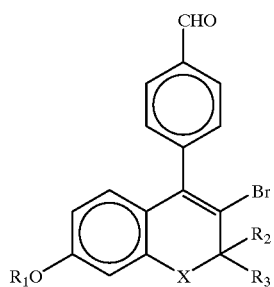
VI
and
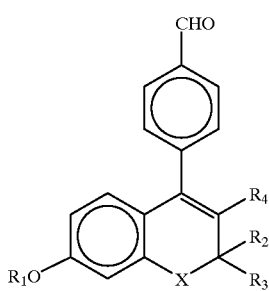
VII
wherein $R_1$, $R_2$, $R_3$, $R_4$ and X are defined as in claim 1.
* * * * *